United States Patent [19]

Uhing

[11] 4,263,230

[45] Apr. 21, 1981

[54] BISPHOSPHONITES

[75] Inventor: Eugene H. Uhing, Pleasantville, N.Y.

[73] Assignee: Stauffer Chemical Company, Dobbs Ferry, N.Y.

[21] Appl. No.: 83,887

[22] Filed: Oct. 11, 1979

[51] Int. Cl.³ .............................................. C07F 9/28
[52] U.S. Cl. .................................. 260/932; 252/400 A
[58] Field of Search ............................................. 260/932

[56] References Cited

U.S. PATENT DOCUMENTS

| | | | |
|---|---|---|---|
| 2,957,931 | 10/1960 | Hamilton et al. | 260/932 |
| 3,005,000 | 10/1961 | Cooper | 260/962 |
| 3,171,818 | 3/1965 | Sander | 260/932 |
| 3,255,145 | 6/1966 | Grahm | 260/30.6 |
| 3,270,092 | 8/1966 | Harwood | 260/937 |
| 3,681,481 | 8/1972 | Lin | 260/932 |
| 3,825,629 | 7/1974 | Hofer et al. | 260/932 |
| 3,845,169 | 10/1974 | Maier | 260/932 |
| 3,875,264 | 4/1975 | Hofer et al. | 260/932 |
| 4,029,721 | 6/1977 | Vollmer et al. | 260/928 |

OTHER PUBLICATIONS

King et al., "Inorganic Chemistry," vol. 17, No. 10, (1978), pp. 2961–2963.

*Primary Examiner*—Anton H. Sutto
*Attorney, Agent, or Firm*—Michael E. Zall

[57] ABSTRACT

Novel bisphosphonite compounds of the formula:

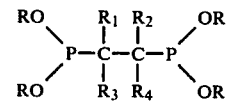

wherein $R_1$, $R_2$, $R_3$ and $R_4$ are each independently selected from the group consisting of hydrogen and alkyl of from 1 to 10 carbon atoms, and R is selected from the group consisting of cyclic, straight or branched chain alkyl of from 5 to 12 carbon atoms, straight or branched chain haloalkyl of from 1 to 12 carbon atoms, phenyl, and alkyl substituted phenyl wherein each alkyl is from 1 to 12 carbon atoms.

The compounds are useful as intermediates for the production of polymers, insecticides, fungicides, pharmaceuticals, catalyst activators, flame retardants and particularly stabilizers, e.g., anti-oxidants.

11 Claims, No Drawings

BISPHOSPHONITES

BACKGROUND OF THE INVENTION

1. Field of the Invention

This invention relates to novel bisphosphonite compounds, and in particular 1,2-bisphosphonite compounds, and their use.

2. Prior Art

U.S. Pat. No. 3,171,818 to Sander describes, for example, the use of "tetramethyl-tetramethylene-diphosphonite", i.e. tetramethyl 1,2-butanebisphosphonite and "tetraethylethylene-diphosphonite", i.e. tetra-ethyl-1,2-ethanebisphosphonite, and other bisphosphonites as intermediates for producing phosphorous containing polymers.

Poly (tertiary phosphines and arsines). 16. Some Metal Carbonyl Complexes of 1,2-bis(dimethoxyphosphino)ethane, Inorganic Chemistry, Vol. 17, No. 10, October, 1978 describes the compound 1,2-bis(dimethoxyphosphino)ethane, i.e. tetra-methyl 1,2-ethanebisphosphonite and its preparation.

Additionally, U.S. Pat. Nos. 3,825,629 and 3,875,264 both to Hofer et al. describe certain bisphosphonite compounds having aromatic substituents between the phosphorus substituents and their preparation.

Of additional interest are: U.S. Pat. No. 3,270,092 to Harwood which describes certain cyclic phosphonites and their preparation; U.S. Pat. No. 3,005,000 to Cooper which describes certain diphenyl phosphonite compounds and their preparation; U.S. Pat. No. 3,255,145 to Graham which describes certain bis [di(beta-halohydrocarbyl)phosphonate]ethane compounds, i.e. pentavalent phosphorus compounds, and their preparation; and U.S. Pat. No. 4,029,721 to Vollmer et al. which describes certain halogen containing phosphoric acid polyester compounds, i.e. pentavalent phosphorus compounds, and their preparation.

SUMMARY OF THE INVENTION

It is an object of this invention to provide for certain novel 1,2-bisphosphonite compounds which are useful as intermediates for the production of polymers, insecticides, fungicides, pharmaceuticals, catalyst activators, flame retardants, and particularly, as stabilizers, e.g., antioxidants.

The novel compounds of this invention are of the formula:

$$\underset{RO}{\overset{RO}{>}}P-\underset{\underset{R_3}{|}}{\overset{\overset{R_1}{|}}{C}}-\underset{\underset{R_4}{|}}{\overset{\overset{R_2}{|}}{C}}-P\underset{OR}{\overset{OR}{<}}$$

wherein $R_1$, $R_2$, $R_3$ and $R_4$ are each independently selected from the group consisting of hydrogen and alkyl of from 1 to 10 carbon atoms, and R is selected from the group consisting of cyclic, straight or branched chain alkyl of from 5 to 12 carbon atoms, straight or branched chain haloalkyl of from 1 to 12 carbon atoms, phenyl, and alkyl substituted phenyl wherein each alkyl is from 1 to 12 carbon atoms.

DETAILED DESCRIPTION OF THE INVENTION

There are several processes for producing the novel compounds of this invention. Generally, these may be be characterized as follows:

FORMULA I

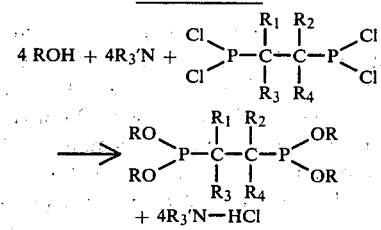

FORMULA II

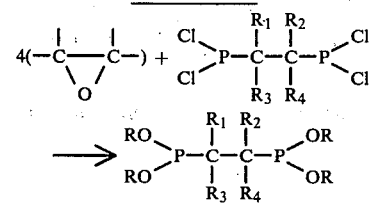

wherein R is

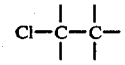

and

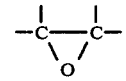

is an appropriate epoxy.

FORMULA III

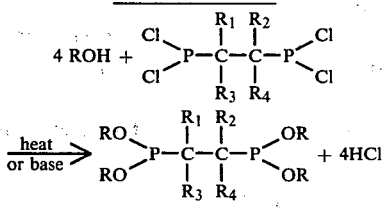

wherein, preferably, R is an aromatic substituent such as phenyl.

The alkane bis-dichlorophosphine, i.e.

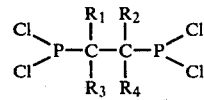

utilized as a key reactant in producing the novel compounds of this invention, is generally prepared by reacting an olefin with phosphorus trichloride, in the presence of elemental phosphorous under at least autogenous pressure at temperatures of from 150° C. to 350° C. More specific details on the preparation of the alkane bis-dichlorophosphine may be found in U.S. Pat. No. 3,976,690 to Toy et al. The entire disclosure of this patent is incorporated herein by reference. The alkane bis-dichlorophosphine used to make the preferred compounds of this invention is 1,2-ethanebisphosphonous dichloride.

Processes for producing similar compounds to the novel compounds of this invention are described in the aforementioned U.S. Pat. Nos. 3,005,000, 3,270,092, 3,825,629 and 3,875,264. The entire disclosures of all of these U.S. patents are incorporated herein by reference. Particularly preferred compounds are those wherein $R_1$, $R_2$, $R_3$ and $R_4$ are all hydrogen. Examples of such preferred compounds are:

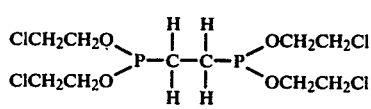

tetra-(2-chloroethyl)-1,2-ethanebisphosphonite.

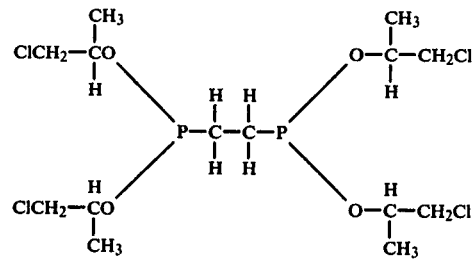

tetra-(1-chloroisopropyl)-1,2-ethanebisphosphonite.

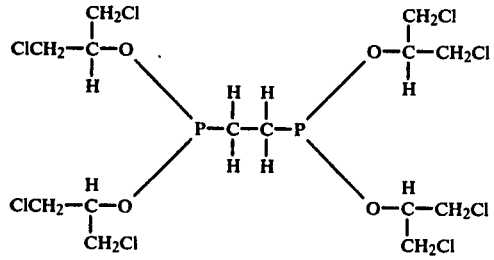

tetra-(1,3 dichloroisopropyl) 1,2-ethanebisphosphonite

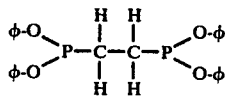

wherein $\phi$ is phenyl. tetra-phenyl-1,2-ethanebisphosphonite.

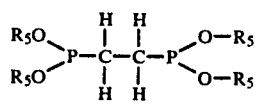

wherein $R_5$ is 2,4-di-tertbutyl phenyl. tetra-(2,4-di-tert-butyl phenyl)-1,2-ethanebisphosphonite

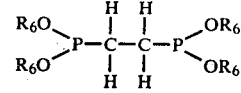

wherein $R_6$ is para-nonyl phenyl. tetra-(para-nonylphenyl)-1,2-ethanebisphosphonite

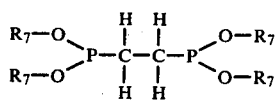

wherein $R_7$ is 2,6-dimethyl phenyl. tetra-(2,6-dimethylphenyl)-1,2-ethanebisphosphonite

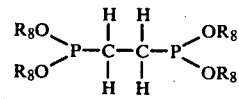

wherein $R_8$ is iso-decyl. tetra-(isodecyl)-1,2-ethanebisphosphonite

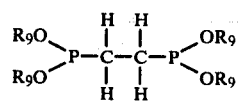

wherein $R_9$ is menthyl. tetra-menthyl-1,2-ethanebisphosphonite. The menthyl substituent has the formula:

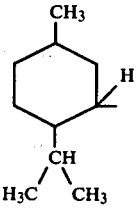

and has optically active isomers, i.e. (−) menthyl and (+) menthyl.

The invention also concerns the use of the compounds of this invention as stabilizers.

For this purpose the new compounds are either incorporated in the product or material sensitive to light, oxygen and heat, or applied to its surface to form a protective film. By their stabilizing effect they protect these sensitive substances from degradation. They have a wide range of application in the processing of plastics; to name some examples, they can be employed as stabilizers for cellulose acetate, cellulose propionate, cellulose acetobutyrate, polyethylene, polypropylene, polyvinyl chloride, polyvinyl chloride-acetate, polyamides, polystyrene, ethyl cellulose, cellulose nitrate, polyvinyl alcohol, silicon rubber, melamine-formaldehyde and unreaformaldehyde resins, allyl case resins, polymethylmethacrylate, polyesters and polyacrylonitrile.

The compounds can also be used to protect natural products such as rubber, cellulose, wool and silk from degradation.

The products of materials for protection may be present in the form of sheet or film, panels, tubing, rods, tapes, coatings, fibres, granules, powders or other solid forms, or as solutions, emulsions of dispersions. The stabilizers are incorporated in, or applied to these materials by the known methods. One of the main methods of application is intimate mixing of the stabilizer and the plastic material, e.g., polypropylene granules, in a kneading or other suitable machine and extrusion moulding of the mixture. This technique ensures homogeneous blending, which is important for effective protection. Extrusion moulding is employed to produce a variety of products, including films, tubing and filaments. The latter can be converted into woven fabrics.

If polypropylene, for instance, is to be processed as woven fabric the stabilizer is normally mixed with it prior to extrusion as filament yarn. However, these new stabilizers can be applied with equally good effect to textile yarns and fabrics, for example from an aqueous bath containing the compound of this invention in superfine dispersion. Textiles of polyester and cellulose acetate fibres are suitable for this exhaust method of application.

The plastics need not necessarily be polymerized when the new compounds are added. The latter can be blended with the monomers or prepolymers prior to the condensation or other polymerization reaction yielding the final polymer.

Besides their use for the stabilization of clear films, plastics and the like, the new stabilizers are suitable for application in or an opaque, semiopaque and translucent materials having a surface which is subject to degradation by light, oxygen and heat. Examples of such materials are foamed plastics, opaque film and sheeting, opaque papers, transparent and opaque pigmented plastics, fluorescent pigments and automobile and furniture polishes, creams, lotions, oils and similar products, which latter group of products may be opaque, clear or translucent.

It is in many cases advantageous to mix the new stabilizers of this invention with other types of light absorbers or stabilizers. Those mixtures of agents have often a synergistic effect and protect the treated materials at the same time in a particularly high degree against ultra violet light, heat and oxidative disintegration.

The present invention concerns also the materials which contain compounds of this invention for stabilization. The incorporation of the new compounds into the materials that need protection can be effected at any stage of processing according to known methods, whereby the amount of added protective agents may vary within wide limits, for instance between 0.01 and 5%, preferably between 0.05 and 1%, related to the materials that need protection.

The following are non-limiting examples of the novel compounds of this invention and their preparation.

EXAMPLE 1

Tetra-(2-Chloroethyl) 1,2-Ethanebisphosphonite

In a 1 liter three neck flask equipped with gas inlet tube, reflux condenser, thermometer and stirrer are placed 237.9 g. of 1,2-ethanebisphosphonous dichloride (1.03 moles) and 100 g. of dichloromethane, as the solvent. The reaction mixture is kept under an atmosphere of nitrogen while 202 g. ethylene oxide (4.58 moles–11% excess) is added as a gas into the liquid reaction mixture. The mixture is kept at a reaction temperature of $-10°$ to $0°$ C. by means of an acetone-solid $CO_2$ bath. After 187 g. of ethylene oxide is added the reaction mixture becomes a solid. The mixture is brought to 5° C., at which temperature the mixture has melted. The remaining ethylene oxide is added. After all the ethylene oxide has been added, the mixture is warmed slowly to 50° C. for 30 minutes. The solvent is then distilled off at a reduced pressure (0.1 mm. Hg) at a liquid temperature of 50° C. The product is a liquid syrup weighing 415.9 g. (99% yield).

Index of refraction: 1.5185 at 25° C.
$^{31}P$-NMR spectra - single resonance at $\delta = 186.0$ ppm.
$^{13}C$-NMR spectra resonances at $\delta = 68.1$ ppm (triplet) 44.9 ppm (singlet) and 26.9 ppm (triplet).

EXAMPLE 2

Tetra-(1-Chloroisopropyl)1,2-Ethanebisphosphonite (and Isomeric 2-Chloropropyl)

In a 1 liter, three neck flask equipped with a stirrer, thermometer, reflux condenser, and dropping funnel, are placed 248 g. of 1,2-ethanebisphosphonous dichloride (1.07 moles) and 200 g. of dichloromethane as the solvent. The reaction mixture is kept under an atmosphere of nitrogen. In the dropping funnel 271 g. of propylene oxide (4.66 moles—9% excess) is placed. The propylene oxide is added dropwise to the flask. The reaction mixture is kept at a temperature of 0°–5° C. by cooling with a dry ice-acetone bath as necessary. The addition of the propylene oxide took 2 hours. After all the propylene oxide is added, the reaction mixture is warmed for one-hour to 45° C. and kept at this temperature for 30 minutes. The solvent is removed by distillation under reduced pressure (0.1 mm. Hg) at a temperature of 45°–50° C. The product is a viscous liquid weighing 493.3 g. (99% yield).

Index of refraction: 1.4982 at 25° C.
Analysis: ($C_{14}H_{28}Cl_4O_9P_2$)
Theoretical: 30.55% Cl.; 13.35% P.
Actual: 30.0% Cl; 13.5% P.
$^{31}P$-NMR spectra-major resonances at $\delta = 184$ ppm. with some closely related resonances indicating that the propylene oxide also formed some of the isomeric 2-chloropropyl derivative.

EXAMPLE 3

Tetra-(1,3-Dichloroisopropyl)-1,2-Ethanebisphosphonite

Using the procedure described in Example 2 270 g. 1,2-ethanebisphosphonous dichloride (1.16 moles) is reacted with 474 g. epichlorohydrin (5.12 moles—10% excess) in 150 g. dichloromethane solvent at a temperature of 0°–10° C. After the addition of the epichlorohydrin, the reaction is warmed slowly to 50° C. The reaction became slightly exothermic and cooling with ice bath was required for about 30 minutes. The solvent is removed by distillation under reduced pressure (0.1 mm. Hg) at a liquid temperature of 60° C. The product crystallized upon cooling. The weight of product was 689 g. (98.7% yield).

Melting point: 55°–60° C.
$^{31}P$-NMR—a single resonance at $= 191.9$ ppm.
$^{13}P$-NMR—resonances at $= 78.98$ ppm. (triplet); 46.28 ppm. (doublet) and 28.64 ppm. (singlet).

EXAMPLE 4

Tetra-Phenyl-1,2-Ethanebisphosphonite

In a 1 liter three neck flask equipped with a stirrer, vacuum distillation head, dropping funnel and thermometer is placed 417 g. phenol (4.43 moles—5% excess) which is warmed to melt. The reaction mixture is kept under an atmosphere of nitrogen. In the dropping funnel is placed 244 g. of 1,2-ethanebisphosphonous dichloride (1.05 moles) which is added to the flask over a 30 minute period. The system is kept under a pressure of 200 mm. Hg by means of an aspirator which also removes the HCl gas formed. The reaction under these conditions is slightly exothermic. Warming is required to maintain the reaction mixture at 35°–40° C. When all the 1,2-ethanebisphosphonous dichloride has been added, the pressure is reduced to 70 mm. Hg. 100 ml. of toluene is placed in the dropping funnel and added as required to keep the reaction mixture from forming a solid. The temperature is raised to 75° C. over a period of 1 hour. Some of the toluene distills off during this period. The mixture is then heated to 75° C. for one hour at a pressure of 15–20 mm. Hg.

The reaction mixture is then vacuum stripped at 0.05 mm. Hg pressure to remove the excess phenol. Product yield is 487.7 g. (theoretical yield-485.6 g.—the product probably contains phenol).

$^{31}$P-NMR spectra—a resonance at $\delta = 179.5$ ppm.

A portion of the product was distilled in a molecular still at 200° C., 0.1 mm. Hg to give a solid product having a melting point of 78°–80° C.

EXAMPLE 5

Tetra-(2,4-Di-Tertbutylphenyl)-1,2-Ethanebisphosphonite

In a 1 liter three neck flask equipped with a stirrer, dropping funnel, reflux condenser with vacuum take off and thermometer, is placed 464.3 g. of 2,4-di-tertbutyl phenol (2.25 moles—2.3% excess). In the dropping funnel is placed 128 g. 1,2-ethanebisphosphonous dichloride (0.55 moles). The flask is heated to melt the 2,4-di-tertbutyl phenol and the flask placed under 20 mm. Hg pressure by means of an aspirator which also removes the HCl formed. The 1,2-ethanebisphosphonous dichloride is added to the reaction flask over a period of 1 hour. The reaction mixture is then heated to 170° C. for 2 hours and the pressure reduced to 1 mm. Hg. The reaction is completed by heating at 225° C. for 4 hours while passing a stream of nitrogen gas through the product at atmospheric pressure.

Product yield is 500 g. (99.8% yield). The product is a colorless solid have a melting point of 95°–115° C.

$^{31}$P-NMR spectra—resonance at $\delta = 171.9$ ppm.

EXAMPLE 6

Tetra-(Para-Nonyl Phenyl)-1,2-Ethanebisphosphonite

In a 1 liter three neck flask equipped with stirrer, nitrogen gas inlet tube, reflux condenser, thermometer and dropping funnel is placed 305 g. of p-nonylphenol (1.38 moles—3% excess). In the dropping funnel is placed 76.6 g. 1,2-ethanebisphosphonous dichloride (0.33 moles). Nitrogen is bubbled through the reaction mixture to help remove the HCl as it forms. The vented nitrogen gas is passed through a water trap to remove the HCl. The reaction is heated to 60°–70° C. while the 1,2-ethanebisphosphonous dichloride is added. The temperature of the reaction mixture is then slowly raised to 190° C. and kept at this temperature for 3 hours. Product yield is 317.5 g. (99.5% yield). The product is a low melting solid.

$^{31}$P-NMR spectra—a single resonance at $\delta = 178.5$ ppm.

EXAMPLE 7

Tetra-(2,6-Dimethylphenyl)-1,2-Ethanebisphosphonite

Using the procedure described in Example 6, 127.06 g. 2,6-dimethylphenol (1.04 moles) is reacted with 58 g. 1,2-ethanebisphosphonous dichloride (0.25 moles) at a temperature of 220° C. The 2,6-dimethyl phenol which sublimes is returned to the reaction mixture. Product yield is 146.5 g. (theoretical yield—143.7 g.). The product is a solid having a melting point of 116°–126° C.

$^{31}$P-NMR spectra—a major resonance at $\delta = 189.9$ ppm.

EXAMPLE 8

Tetra-(Isodecyl)-1,2-Ethanebisphosphonite

In a 1 liter three neck flask equipped with a mechanical stirrer, dropping funnel, reflux condenser and thermometer is placed 189.9 g. iso-decyl alcohol (1.2 moles), 133 g. triethylamine (1.31 m.) and 300 g. of dichloromethane as a solvent. The reaction mixture is kept under an atmosphere of nitrogen. In the dropping funnel is placed 69.6 g. 1,2-ethanebisphosphonous dichloride (0.3 moles) diluted with an equal weight of dichloromethane. The reaction mixture is kept at $-10°$ to 0° C. while the 1,2-ethanebisphosphonous dichloride solution is added dropwise. After the addition of the reaction mixture is allowed to warm to room temperature. The reaction mixture is filtered to remove the solid triethylamine hydrochloride which is formed. The solvent is removed from the filtrate by distillation under reduced pressure. The final traces of triethylamine hydrochloride are removed by dissolving the product in heptane and filtering. The filtrate is then vacuum stripped of solvent at 100° C. and a pressure of 0.1 mm. Hg.

Product yield is 192 g. or 88.8% yield.

$^{31}$P-NMR spectra—one resonance of $\delta = 180.8$ ppm.

Index refraction is 1.4669 at 25° C.

EXAMPLE 9

Tetra((−)Menthyl)-1,2-Ethanebisphosphonite

To a 1 liter three neck flask equipped with a mechanical stirrer, addition funnel, reflux condenser and thermometer was added 300 mls. of anhydrous diethyl ether, 62.5 g. (0.4 moles), 62.5 g. (0.4 moles) of (−) menthol and 44 g. (0.44 moles) of triethyl amine. The solution was kept under nitrogen as 23 g. (0.1 moles) of 1,2-ethanebisphosphonous dichloride was added. As the addition of the dichloride proceeded, the temperature of the reaction rose from 25° C. The pot contents were then cooled with an ice/water bath to maintain 25° C. After complete addition of the dichloride, the pot contents were stirred for six hours at 25° C. The by-product, triethyl amine hydrochloride, was then vacuum filtered from the reaction mixture under a nitrogen atmosphere, washed with 100 mls. of diethyl ether and filtered again. The filtrates were combined and the solvent stripped at reduced pressure (50 mm. Hg) under steam heat. The product, a light yellow, viscous liquid was obtained at 99% yield.

The $^{31}$P-NMR analysis showed a major resonance of $\delta = 180.7$ ppm., typical of a phosphonite ester, accounting for 98.4% of all phosphorus resonances observed for the product.

EXAMPLE 10

Tetra((+)-Menthyl)-1,2-Ethanebisphosphonite

The same procedure as Example 9 was used, except (+) menthol was used. A 99% yield was obtained.

The $^{31}$P-NMR analysis showed a major resonance of $\delta -178.5$ ppm., typical of a phosphonite ester, accounting for 97.7% of all phosphorus resonance observed for the product.

EXAMPLE 11

Inhibition of Oxidation

The compounds of Examples 4, 5 and 6 were tested to determine their ability to inhibit oxidation, i.e. anti-oxidant properties, both alone and in conjunction with Ethyl Antioxidant 702[1], a hindered phenol type antioxidant. The following procedures were used:

[1] Tradename of Ethyl Corporation, Baton Rouge, Louisiana for 4,4'-methylenebis 2,6-di-tert-butylphenol.

PROCEDURE I 1.0 ml. samples (by pipet) of blends of polydecene were placed in the covers of 60×15 mm. Petri dishes so as to cover the entire bottom of the dish with oil. The dishes were then placed in a thermostatically controlled oven at 200° C., which was slowly flushed with air. The samples were removed after 1 hour and i.r. spectra taken. The ratio of the absorbance maximum at 1730 cm$^{-1}$ (C=O, due to oxidation of the oil) to those at 1480 cm$^{-1}$ (C—H, essentially invariant with same sample size regardless of degree of oxidation) were measured and recorded as "R". The higher the value of "R", the more oxidized is the oil.

PROCEDURE II

Same procedure as Procedure I, except that 2.0 ml. samples were heated for 2 hours at 200° C.

RESULTS

| PROCEDURE I | |
|---|---|
| Additives (By % Weight) | R |
| (a) None | .48 |
| (b) 0.1% Ethyl 702 | .39 |
| (c) 0.2% Ethyl 702 | .13 |
| (d) 0.1% Example 5 compound | .43 |
| (e) 0.1% Example 6 compound | .21 |
| (f) 0.1% each of Ethyl 702 and Example 5 compound | .11 |
| (g) 0.1% each of Ethyl 702 and Example 6 compound | .21 |

| PROCEDURE II | |
|---|---|
| Additive (% By Weight) | R |
| None | .46 |
| 0.1% Ethyl 702 | .37 |
| 0.2% Ethyl 702 | .15 |
| 0.1% Example 4 compound | .44 |
| 0.1% Example 5 compound | .35 |
| 0.1% Example 6 compound | .32 |
| 0.1% each of Ethyl 702 and Example 4 compound | .21 |
| 0.1% each of Ethyl 702 and Example 5 compound | .23 |
| 0.1% each of Ethyl 702 and Example 6 compound | .29 |

EXAMPLE 12

Antioxidant Synergist Utilty in Polypropylene

The compound of Example 5 was mixed with IRGANOX 1010, a hindered phenol antioxidant, (Ciba-Geigy Corporation) having the structure:

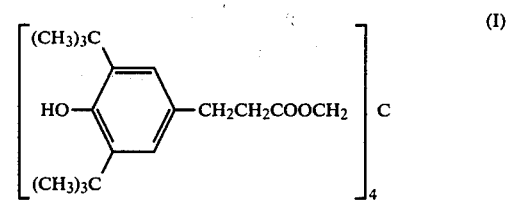

in polypropylene. Both compounds were present at 0.1 wt. % (I) A polypropylene mixture with only 0.1% IRGANOX 1010 was also prepared (II). The polypropylene used was previously purified by washing with acetone and the isopropanol. Mixing was accomplished in a Brabender torque rheometer, a standard polymer laboratory device which consists of a thermostatted mixing chamber having rotating kneader blades which turn at a constant number of revolutions per minute. The torque required to mix and stir the plastic mass is measured, and serves as a measure of the polymer viscosity and thus of the polymer stability. Oxidative breakdown of the polymer causes loss of molecular weight, a drop in viscosity, and consequently a lower torque requirement.

At 205° C. and 90 RPM, after 20 minutes, the torque measurement (viscosity) of II was 580 M. gm. (metergrams); and of I was 660 M. gm. At 205° C. and 100 RPM, the torque measurement of II dropped to 710 M. gm., whereas I was 820 M. gm. These results indicate that the compound of this invention is useful as a polymer stabilizer in conjunction with conventional hindered phenol antioxidants.

What is claimed is:

1. A compound of the formula:

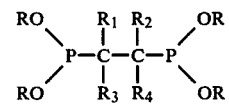

wherein R$_1$, R$_2$, R$_3$ and R$_4$ are each hydrogen, and R is selected from the group consisting of straight or branched chain haloalkyl of from 1 to 12 carbon atoms, phenyl, and alkyl substituted phenyl wherein each alkyl is from 1 to 12 carbon atoms.

2. The compound of claim 1, wherein R is straight or branched chain chloroalkyl of from 1 to 12 carbon atoms.

3. The compound of claim 1, wherein R is phenyl.

4. The compound of claim 1, wherein R is alkyl substituted phenyl wherein each alkyl is from 1 to 12 carbon atoms.

5. A compound of the formula:

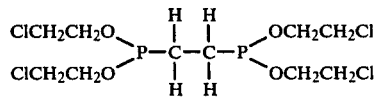

6. A compound of the formula:

7. A compound of the formula:
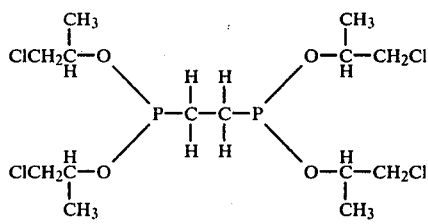
8. A compound of the formula:
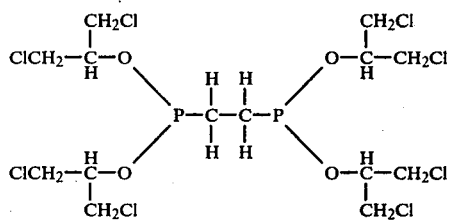
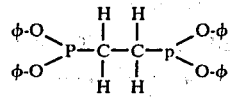
wherein φ is phenyl.
9. A compound of the formula:
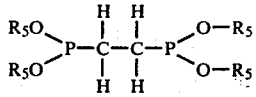
wherein $R_5$ is 2,4-di-tertbutyl phenyl.
10. A compound of the formula:
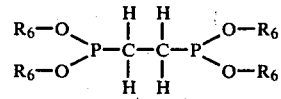
wherein $R_6$ is para-nonyl phenyl.
11. A compound of the formula:
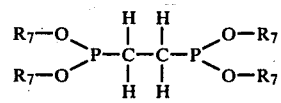
wherein $R_7$ is 2,6-dimethyl phenyl.
* * * * *

UNITED STATES PATENT AND TRADEMARK OFFICE
CERTIFICATE OF CORRECTION

PATENT NO. : 4,263,230
DATED : April 21, 1981
INVENTOR(S) : Eugene H. Uhing

It is certified that error appears in the above-identified patent and that said Letters Patent are hereby corrected as shown below:

Formula 1, Col. 2, "$R_3'$" should be -- $R'_3$ --;

Col. 4, line 60, "unreaforaldehyde" should be -- ureaformaldehyde --;

Col. 9, Example 10, "$\int - 178.5$" should be -- $\int = 178.5$ --.

Signed and Sealed this

Twenty-fifth Day of August 1981

[SEAL]

*Attest:*

GERALD J. MOSSINGHOFF

*Attesting Officer*     *Commissioner of Patents and Trademarks*